US00PP36230P2

(12) United States Plant Patent
Van Swieten

(10) Patent No.: US PP36,230 P2
(45) Date of Patent: Oct. 29, 2024

(54) ***PHALAENOPSIS* ORCHID PLANT NAMED 'PHA279943'**

(50) Latin Name: ***Phalaenopsis* hybrid**
Varietal Denomination: PHA279943

(71) Applicant: ANTHURA B.V., Bleiswijk (NL)

(72) Inventor: Martinus Nicolaas Gerardus Van Swieten, Utrecht (NL)

(73) Assignee: Anthura B.V., Bleiswijk (NL)

( * ) Notice: Subject to any disclaimer, the term of this patent is extended or adjusted under 35 U.S.C. 154(b) by 0 days.

(21) Appl. No.: 18/831,073

(22) Filed: Jun. 6, 2024

(51) Int. Cl.
*A01H 5/02* (2018.01)
*A01H 6/62* (2018.01)

(52) U.S. Cl.
USPC ..... Plt./311
CPC ..... *A01H 6/62* (2018.05)

(58) Field of Classification Search
USPC ..... Plt./311
CPC ..... A01H 5/02
See application file for complete search history.

*Primary Examiner* — Kent L Bell
(74) *Attorney, Agent, or Firm* — Jondle & Associates, P.C.

(57) ABSTRACT

A new and distinct variety of *Phalaenopsis* plant named 'PHA279943', particularly characterized by having few branches and numerous attractive, small, orange striped and netted flowers with red lips, concave flowers, and concave apical lobe lips in lateral view, and is propagated by meristem tissue culture, is disclosed.

3 Drawing Sheets

Genus and species: *Phalaenopsis* hybrid.
Variety denomination: 'PHA279943'.

BACKGROUND OF THE NEW PLANT

The present invention relates to a new and distinct cultivar of *Phalaenopsis* plant, botanically known as *Phalaenopsis* hybrid of the Orchidaceae family, commonly referred to as moth orchid, and hereinafter referred to by the variety name 'PHA279943'.

The new *Phalaenopsis* plant is a product of a planned breeding program conducted by the inventor in Bleiswijk, the Netherlands. The objective of this breeding program was to create a new *Phalaenopsis* plant with a few branches and numerous attractive, small, orange striped and netted flowers with red lips suitable for potted plant production.

The new *Phalaenopsis* plant 'PHA279943' is a result of cross-pollination made by the inventor in November 2014 in Bleiswijk, the Netherlands, of the proprietary female, or seed parent, *Phalaenopsis* hybrid '24-E02150-0001' (unpatented) with the proprietary male, or pollen parent, *Phalaenopsis* hybrid '24-E02151-0001' (unpatented).

The new *Phalaenopsis* was selected by the inventor as a single plant within the progeny of the stated cross-pollination in a controlled greenhouse in Bleiswijk, the Netherlands, in August 2018. Asexual reproduction of the new *Phalaenopsis* plant by meristem tissue culture since 2019 in Bleiswijk, the Netherlands, has demonstrated that the new variety reproduces true to type with all the characteristics, as herein described, firmly fixed and retained through successive generations.

Plant Breeders' Rights or Community Plant Variety Rights have not been filed for this variety. 'PHA279943' has not been made publicly available or sold anywhere in the world prior to the effective filing date of this application with the exception of sales or disclosures made one year or less before the effective filing date of this claimed invention by Applicant who obtained 'PHA279943' directly from the inventor.

SUMMARY OF THE INVENTION

The following are the most outstanding and distinguishing characteristics of this new cultivar when grown under normal horticultural practices in Bleiswijk, the Netherlands, and can be used to distinguish 'PHA279943' as a new and distinct variety of *Phalaenopsis* plant:

1. Small, orange striped and netted flowers with red lips;
2. Flower: shape in lateral view is concave;
3. Lip: curvature of lateral lobe is medium; and
4. Lip: apical lobe in lateral view is concave.

DESCRIPTION OF THE PHOTOGRAPHS

This new *Phalaenopsis* plant is illustrated by the accompanying photographs which show the overall plant habit including blooms, buds, and foliage of the plant; the colors shown are as true as can be reasonably obtained by conventional photographic procedures. The photographs were taken in a greenhouse in Bleiswijk, the Netherlands, from 50-week-old plants in April 2024. Colors in the photographs may differ from the color values cited in the detailed botanical description, which accurately describe the actual colors of the new variety.

DESCRIPTION OF THE NEW VARIETY

Figure 1:
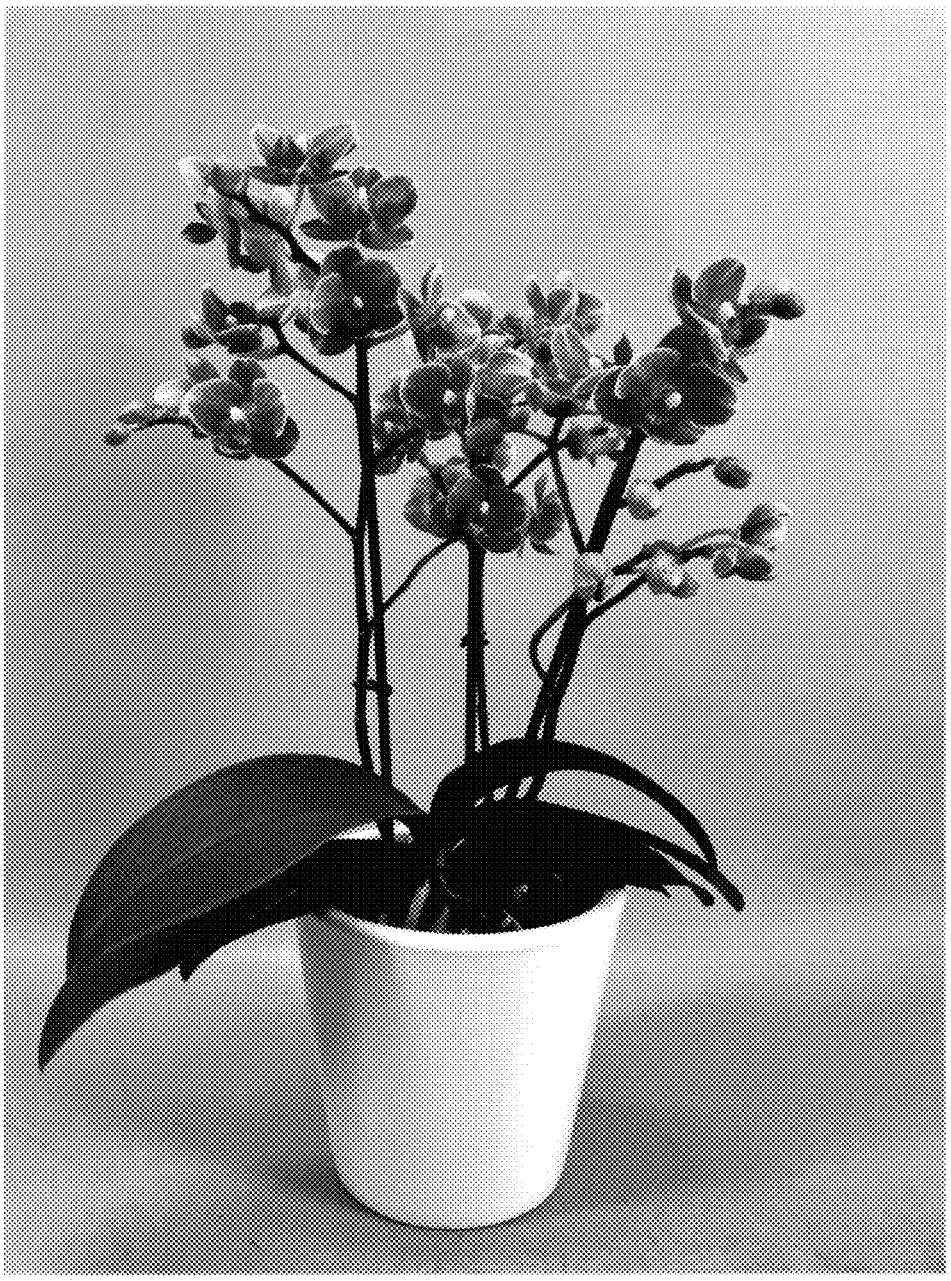
FIG. 1 shows the overall plant habit, including blooms, buds, and foliage of 'PHA279943'.
Figure 2:
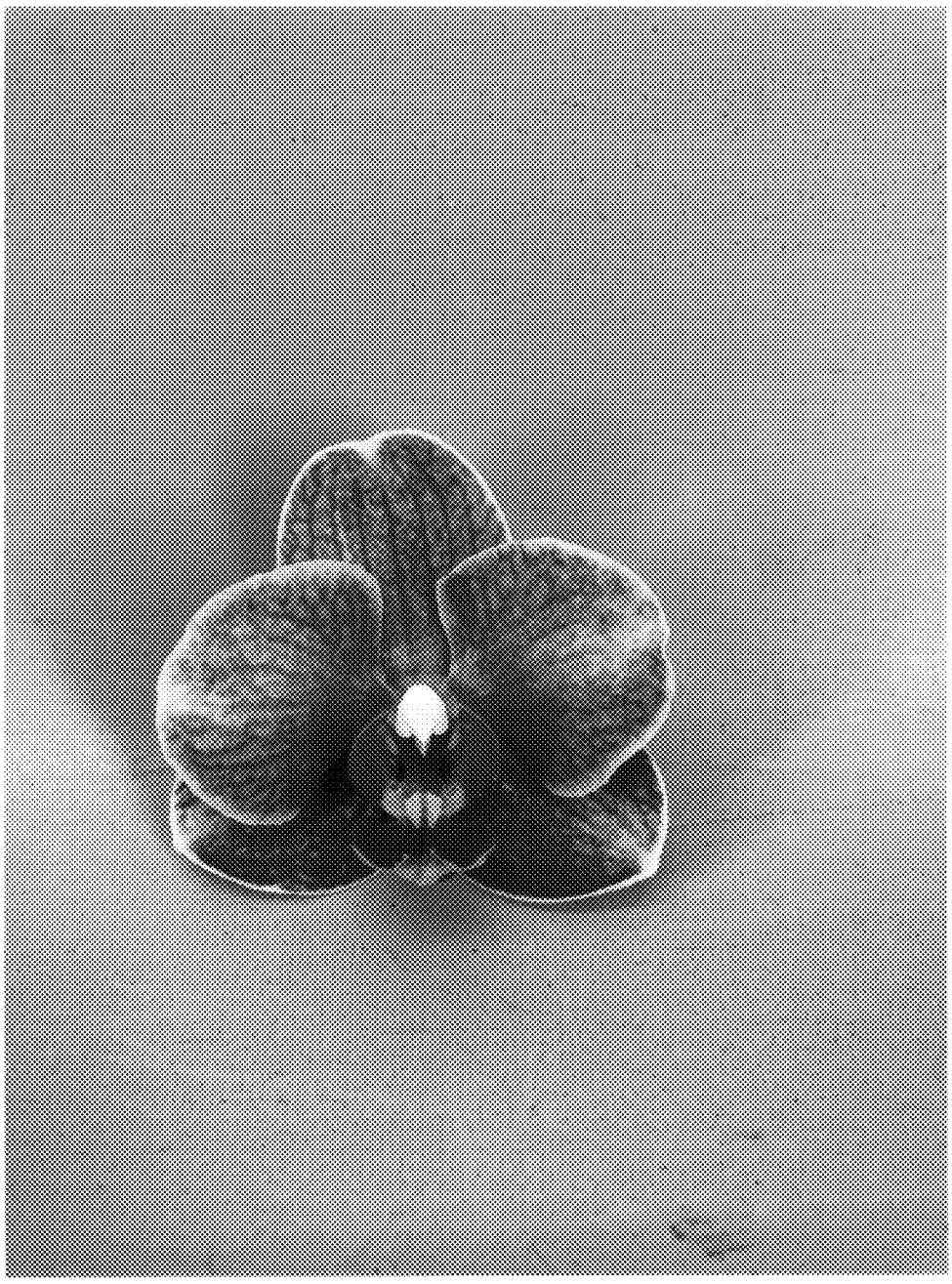
FIG. 2 shows a close-up of a flower of 'PHA279943'.
Figure 3:
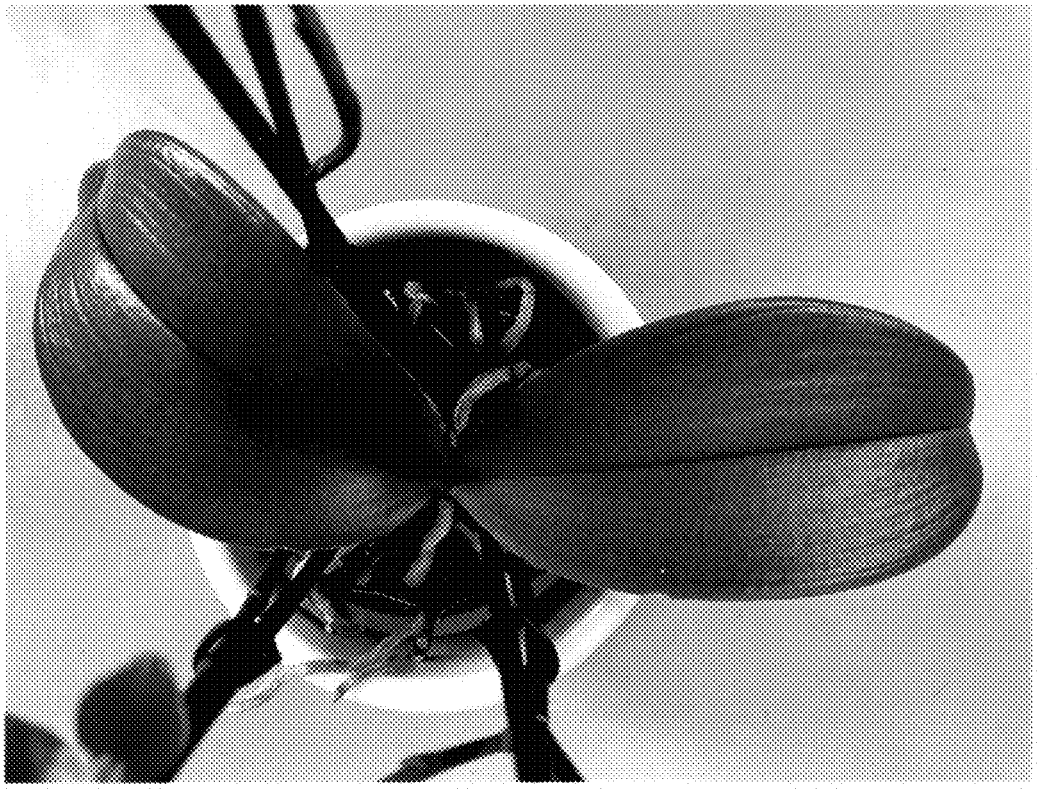
FIG. 3 shows an overhead, close-up view of the leaves of 'PHA279943'.

The following detailed description sets forth the distinctive characteristics of 'PHA279943'. Plants of the new

*Phalaenopsis* have not been observed under all possible environmental conditions. The phenotype may vary somewhat with variations in environment such as temperature, light intensity, and day length, without, however, any variance in genotype. The chart used in the identification of colors described herein is The R.H.S. Colour Chart of The Royal Horticultural Society, London, England, 2015 edition, except where general color terms of ordinary significance are used. The color values were determined under 4000-6000 lux natural light in a greenhouse in Bleiswijk, the Netherlands. Observations and measurements were made in April 2024 on flowering plants which were planted in 12-centimeter (diameter) pots. After in vitro propagation, the plants were grown in nursery trays for 20-24 weeks, followed by transplantation to 12-centimeter pots and grown in a greenhouse between 27° C. to 29° C. for 30 weeks, continued by a cooling period of 8 weeks between 18° C. to 20° C. and 12 weeks in a greenhouse of 21° C. Flowering occurs after 50 weeks in 12-centimeter pots.

DETAILED BOTANICAL DESCRIPTION

Classification:

*Family*.—Orchidaceae.

*Botanical*.—*Phalaenopsis* hybrid.

*Common name*.—Moth orchid.

*Variety name*.—'PHA279943'.

Parentage:

*Female parent*.—*Phalaenopsis* cultivar '24-E02150-0001' (unpatented).

*Male parent*.—*Phalaenopsis* cultivar '24-E02151-0001' (unpatented).

Propagation:

*Type*.—Meristem tissue culture.

Roots:

*Root description*.—Greyed-green colored roots (a color in between RHS 190B and RHS 190C) with branching lateral roots having orange-yellow colored root tips (RHS 164B).

Plant:

*Crop time to flowering*.—Following asexual propagation (in vitro), the rooted cuttings grow for 20-24 weeks. After transplantation into 12-cm pots, the plants are finished after 48 to 50 weeks.

*Growth habit of the peduncle*.—Upright to slightly pendent with panicle inflorescence.

*Height (from soil level to top of inflorescence)*.—Approximately 30.0 cm to 35.0 cm.

*Width (measured from leaf tips)*.—About 27.0 cm to 29.0 cm.

*Vigor*.—Strong.

Leaves:

*Mature leaves*.—Quantity per plant: 9 to 10 leaves are produced before flowering. Length (fully expanded): 15.0 cm to 18.0 cm. Width: 6.5 cm to 7.5 cm. Position of the broadest part of the leaf: At the middle. Shape: Oblong. Base shape: Moderately elongated. Apex: Obtuse asymmetric. Leaf blade angle with the petiole (measured from the horizontal position): Between 5 degrees and 15 degrees. Leaf margin: Entire. Color: Upper surface: Green (RHS 147A). Lower surface: Green (RHS 146A) with a touch of dark purple-red (RHS N186C) towards margins. Texture (both upper and lower surfaces): Smooth. Thickness: 2.0 mm to 3.0 mm. Variegation: Absent. Venation: Pattern: Parallel. Color of the midvein: Upper surface: Green (RHS 147A). Lower surface: Dark purplish-red (RHS N186C).

Peduncle:

*Quantity per plant*.—3.

*Number of flowers per peduncle*.—17 to 23.

*Length*.—30.0 cm to 35.0 cm.

*Diameter*.—4.0 mm to 5.0 mm.

*Strength*.—Strong.

*Aspect*.—Upright to slightly pendent.

*Texture*.—Smooth.

*Color*.—Mix of light yellow-green (a color in between RHS 146B and RHS 146C) and brown (a color in between RHS 200A and RHS N186C).

*Internode length*.—2.0 cm to 2.5 cm.

Inflorescence description:

*Appearance*.—Upright to slightly pendent, panicle inflorescence with bilaterally symmetrical flowers that open in succession beginning with the lowermost flower.

*Number of inflorescences*.—3.

*Inflorescence size*.—Height (from base to tip).—150.0 mm to 200.0 mm.

*Flowering time*.—First flowers can be expected 10 to 11 months after planting in a 12-cm pot.

*Flower*.—Height: 46.0 mm to 48.0 mm. Diameter: 45.0 mm to 50.0 mm. Depth of lip: 15.0 mm to 17.0 mm.

*Flower shape*.—Concave.

*Flower longevity*.—On the plant: 10 to 12 weeks.

*Fragrance*.—Absent.

*Flower bud*.—Average size: Medium. Length: 16.0 mm to 18.0 mm. Width: 16.0 mm to 18.0 mm. Shape: Egg shaped. Color: Greenish-yellow (RHS 151A) with a touch of red (RHS 183B).

*Petals*.—Arrangement: Open/free. Shape: Moderately compressed to medium. Apex: Rounded asymmetric. Margin: Moderately undulated. Length (from base to tip): 19.0 mm to 21.0 mm. Width: 22.0 mm to 24.0 mm. Position of the broadest part of the petal: Toward the base. Color (when fully opened): Upper surface: Basic color: Greenish-yellow (RHS 3C). Over color: Reddish-orange (RHS 178D). Lower surface: Basic color: Greenish-yellow (RHS 3C). Over color: Diluting red shade and stripes (RHS 181C) toward margins. Number of spots, dots, and stripes on the petals (upper surface): Medium stripes. Color of spots, dots, and stripes on the petals (upper surface): RHS 59C. Density of netting of the petals (upper surface): Low. Color of the netting (upper surface): RHS 59C.

*Dorsal sepal*.—Shape: Broad elliptic. Apex: Emarginated symmetric. Margin: Entire. Length (from base to tip): 22.0 mm to 24.0 mm. Width: 19.0 mm to 21.0 mm. Position of the broadest part of the dorsal sepals: At the middle. Color (when fully opened): Upper surface: Basic color: Greenish-yellow (RHS 3C). Over color: Reddish-orange (RHS 178C). Lower surface: Basic color: Greenish-yellow (RHS 3C). Over color: Red (RHS 181C) toward margins. Number of spots, dots, and stripes on the dorsal sepals (upper surface): Many stripes. Color of spots, dots, and stripes on the dorsal sepals (upper surface): RHS 59C. Density of netting of the dorsal sepals (upper surface): Medium. Color of the netting (upper surface): RHS 59C.

*Lateral sepals*.—Shape: Broad ovate. Apex: Obtuse asymmetric. Margin: Entire. Length (from base to tip): 25.0 mm to 27.0 mm. Width: 19.0 mm to 21.0 mm. Position of the broadest part of the lateral sepals: Toward the base. Color (when fully opened): Upper surface: Basic color: Greenish-yellow (RHS 3C). Over color: Reddish-orange (a color in between RHS 178B and RHS 178C). Lower surface: Basic color: Greenish-yellow (a color in between RHS 151C and RHS 1C). Over color: Red (RHS 181C) toward margins. Number of spots, dots, and stripes on the lateral sepals (upper surface): Medium spots at the base; medium stripes. Color of spots, dots, and stripes on the lateral sepals (upper surface): Stripes RHS 59B and spots RHS 59A. Density of netting of the lateral sepals (upper surface): Medium. Color of the netting (upper surface): RHS 59C.

Labellum (lip).—Whiskers: Present, but very short. Length of whiskers: About 1.0 mm. Color of whiskers: Yellow (RHS 13A). Pubescence on the lip: Absent.

*Lateral lobe*.—Shape: Type IV (as described in the International Union for the Protection of New Varieties of Plants (UPOV) Test Guidelines for *Phalaenopsis*); weakly spatulate. Margin: Moderately undulated. Length: 11.0 mm to 13.0 mm. Width: 5.0 mm to 7.0 mm. Color: Upper surface: Yellow (RHS 7B) at the base with few spots RHS 171A and stripes RHS 59B; red (a color in between RHS 180A and RHS 180B); purplish-red (RHS 59C) toward tip. Lower surface: Creamy (RHS 158B) at the base; red (RHS 180B) toward one margin and purplish-red (RHS 59C) toward tip. Number of spots and stripes on the lateral lobe: Few stripes and few spots. Color of spots and stripes on the lateral lobe: Stripes RHS 59B and spots (RHS 171A). Density of netting of the lateral lobe: None. Color of the netting: None.

*Apical lobe*.—Shape: Circular to elliptic. Margin: Entire. Length: 14.0 mm to 16.0 mm. Width: 17.0 mm to 19.0 mm. Color: Upper surface: Red (RHS 176B); reddish-purple (RHS N78B) toward whiskers. Lower surface: Orange (RHS 172B); touch of white (RHS N155C) at the middle toward tip; reddish-purple (RHS N78B) at the middle toward whiskers. Number of spots and stripes on the apical lobe: None. Color of spots and stripes on the apical lobe: Not applicable. Density of netting of the apical lobe: None. Color of the netting: Not applicable. Bump and ridge: Present (small).

*Callus*.—Average size: Small. Height: 3.0 mm to 4.0 mm. Length: 3.0 mm to 4.0 mm. Width: 2.0 mm to 3.0 mm. Color: Light yellow (RHS 12C) on sides; yellow (RHS 14A) toward tips; orange (RHS 178C) dots.

Reproductive organs:

*Column*.—Length: 7.0 mm to 9.0 mm. Diameter: 3.0 mm to 4.0 mm. Color: Light purple (RHS 76A) with white tips (RHS NN155C).

*Pollinia*.—Quantity: 2. Diameter: 0.8 mm to 1.0 mm. Color: Orange-yellow (RHS 23A).

*Ovary*.—Length: 7.0 mm to 9.0 mm. Diameter: 1.7 mm to 2.0 mm.

*Pedicel*.—Length: 27.0 mm to 29.0 mm. Diameter: 2.2 mm to 2.5 mm. Color: Light yellow-green (RHS 145C) and lighter yellow-green (RHS 145D) toward the flower. Texture: Smooth.

Disease, pest, and stress resistance: No specific resistance or susceptibility observed to pathogens and pests common to *Phalaenopsis* to date.

Fruit and seeds: Fruit and seed development has not been observed on plants of the new *Phalaenopsis* to date.

COMPARISON WITH PARENTAL LINES AND MOST SIMILAR VARIETIES

'PHA279943' differs from the female parent plant '24-E02150-0001' (unpatented) in that 'PHA279943' has semi-dropping leaves, emarginated apexes of the dorsal sepal, and the basic color of the petals' upper surface is greenish-yellow, whereas '24-E02150-0001' has semi-erect to horizontal leaves, obtuse apexes of the dorsal sepal, and the basic color of the petals' upper surface is white.

'PHA279943' differs from the male parent plant '24-E02151-0001' (unpatented) in that 'PHA279943' has emarginated apexes of the dorsal sepal, and the over color of the upper surface petals is reddish-orange, whereas '24-E02151-0001' has obtuse apexes of the dorsal sepal, and the over color of the upper surface petals is dark red.

'PHA279943' is most similar to the commercial *Phalaenopsis* plants named 'PHALGURZON' (U.S. Plant Pat. No. 31,708) and 'PHALHUCAR' (U.S. Plant Pat. No. 32,955). 'PHA279943' differs from the commercial variety 'PHALGURZON' in that 'PHA279943' has semi-dropping leaves and more narrow flowers in the front view, whereas 'PHALGURZON' has semi-erect to horizontal leaves and much wider flowers in the front view.

'PHA279943' differs from the commercial variety 'PHALHUCAR' in that 'PHA279943' has very short whiskers, narrow flowers, semi-dropping leaves, and yellow-dotted calli, whereas 'PHALHUCAR' does not have whiskers, has wider flowers, semi-erect to horizontal leaves, and reddish-purple calli.

I claim:

1. A new and distinct variety of *Phalaenopsis* plant named 'PHA279943', substantially as described and illustrated herein.

* * * * *